US006998236B2

(12) United States Patent
Shao et al.

(10) Patent No.: US 6,998,236 B2
(45) Date of Patent: Feb. 14, 2006

(54) METHODS FOR DETECTING INTERACTION BETWEEN A TEST MOIETY AND A PLURALITY OF TARGET MOIETIES

(75) Inventors: Wei Shao, Nanjing (CN); Junquan Xu, San Diego, CA (US); Wan-Li Xing, Beijing (CN); Jing Cheng, Beijing (CN)

(73) Assignees: Capitalbio Corporation, (CN); Tsinghua University, (CN)

( * ) Notice: Subject to any disclaimer, the term of this patent is extended or adjusted under 35 U.S.C. 154(b) by 474 days.

(21) Appl. No.: 10/212,917

(22) Filed: Aug. 5, 2002

(65) Prior Publication Data

US 2002/0187509 A1     Dec. 12, 2002

Related U.S. Application Data

(62) Division of application No. 09/898,271, filed on Jul. 2, 2001, now Pat. No. 6,703,203.

(30) Foreign Application Priority Data

Jul. 4, 2000   (CN) .............................. 00109792 A

(51) Int. Cl.
   *C12Q 1/68*   (2006.01)
   *C12M 1/36*   (2006.01)
   *G01N 31/22*  (2006.01)

(52) U.S. Cl. .......................... 435/6; 435/7.1; 435/174; 435/283.1; 435/287.2; 422/68.1; 422/102

(58) Field of Classification Search .................... 435/6, 435/7.1, 174, 283.1, 287.2; 422/68.1, 102
See application file for complete search history.

(56) References Cited

U.S. PATENT DOCUMENTS

| 5,545,531 | A |   | 8/1996  | Rava et al. .................. 435/6    |
|-----------|---|---|---------|----------------------------------------|
| 5,716,459 | A |   | 2/1998  | Chang et al. ................ 136/249  |
| 5,783,148 | A | * | 7/1998  | Cottingham et al. .......... 422/56    |
| 5,928,437 | A |   | 7/1999  | Dillard ........................ 136/244 |
| 5,930,117 | A |   | 7/1999  | Gengel ........................ 361/720 |
| 6,004,755 | A |   | 12/1999 | Wang ............................. 435/6 |
| 6,093,370 | A |   | 7/2000  | Yasuda et al. ............. 422/68.1   |
| 6,101,946 | A |   | 8/2000  | Martinsky ................... 101/494  |
| 6,142,681 | A |   | 11/2000 | Gulati ......................... 395/13  |
| 6,215,894 | B1|   | 4/2001  | Zeleny et al. ............... 382/133   |
| 6,232,066 | B1| * | 5/2001  | Felder et al. .................. 435/6 |
| 6,245,511 | B1|   | 6/2001  | Gulati .......................... 435/6  |

(Continued)

FOREIGN PATENT DOCUMENTS

CN          1248702          3/2000

(Continued)

OTHER PUBLICATIONS

Beattie et al., Molecular Biotechnology (1995) 4:213-225.

(Continued)

*Primary Examiner*—BJ Forman
(74) *Attorney, Agent, or Firm*—Morrison & Foerster LLP

(57) ABSTRACT

This invention relates generally to the field of microarray technology. In particular, the invention provides an integrated microarray device, which device comprises a substrate comprising a plurality of distinct microlocations and a plurality of microarray chips, wherein the number of said microlocations equals to or is more than the number of said microarray chips. In preferred embodiments, the devices also comprises a temperature controller at some or all of the microlocations. The use of the integrated microarray devices for detecting interactions among various moieties in various fields, such as clinical diagnostics, drug discovery, environmental monitoring and forensic analysis, etc., are further provided.

46 Claims, 3 Drawing Sheets

U.S. PATENT DOCUMENTS

| | | | |
|---|---|---|---|
| 6,258,593 B1 | 7/2001 | Schembri et al. | 435/287.2 |
| 6,355,491 B1 | 3/2002 | Zhou et al. | 436/518 |
| 6,403,367 B1 | 6/2002 | Cheng et al. | 435/287.1 |

FOREIGN PATENT DOCUMENTS

| | | |
|---|---|---|
| CN | 1255552 | 6/2000 |
| CN | 1255651 | 6/2000 |
| WO | WO 00/61817 | 10/2000 |

OTHER PUBLICATIONS

Becker et al., Sensors Update (1998) 3:208-238.
Delamarche et al., J. Am. Chem. Soc. (1998) 120:500-508.
Fodor et al., Science (1991) 251:767-773.
Hacia et al., Nature Genetics (1996) 14:441-447.
Heller et al., Proc. Natl. Acad. Sci. USA (1997) 94:2150-2155.
Kopp et al., Current Opinion in Chemical Biology (1997) 1:410-419.
Simpson et al., Proc. Natl. Acad. Sci. USA (1998) 95:2256-2261.
Subramanian et al., Enzyme and Microbial Technol. (1999) 24:26-34.
Beattie et al., Molecular Biotechnology (1995) 4:213-225.
Becker et al., Sensors Update (1998) 3:208-238.

* cited by examiner

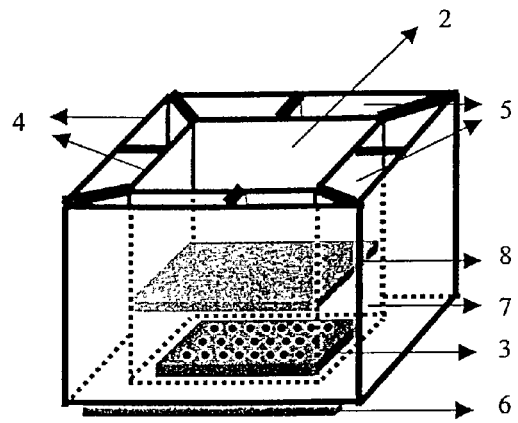
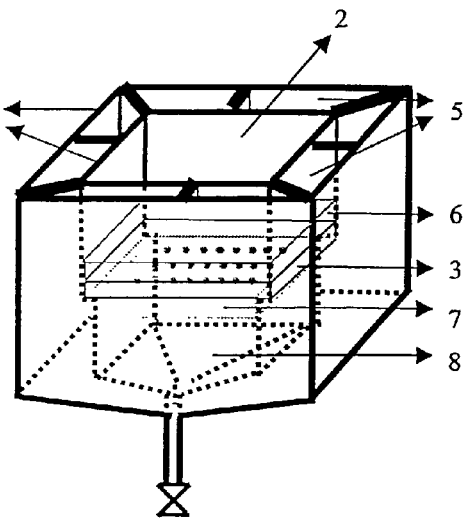
Figure 2A
Figure 2B
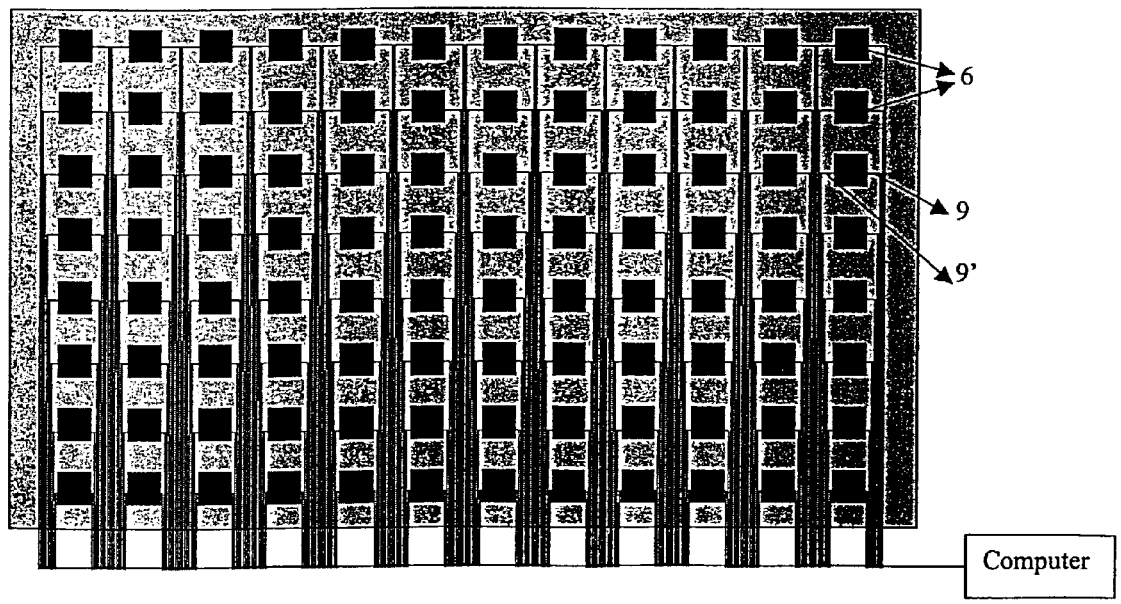
Figure 3

METHODS FOR DETECTING INTERACTION BETWEEN A TEST MOIETY AND A PLURALITY OF TARGET MOIETIES

RELATED APPLICATION

The present application is a divisional application of U.S. patent application Ser. No. 09/898,271, filed Jul. 2, 2001, now U.S. Pat. No. 6,703,203, which claims priority to related Chinese national patent application Ser. No. 00109792.X, filed Jul. 4, 2000, entitled "INTEGRATED MICROARRAY DEVICES," the contents of which are incorporated by reference in their entirety.

TECHNICAL FIELD

This invention relates generally to the field of microarray technology. In particular, the invention provides an integrated microarray device, which device comprises a substrate comprising a plurality of distinct microlocations and a plurality of microarray chips, wherein the number of said microlocations equals to or is more than the number of said microarray chips. In preferred embodiments, the devices also comprise a temperature controller at some or all of the microlocations. The use of the integrated microarray devices for detecting interactions among various moieties in various fields, such as clinical diagnostics, drug discovery, environmental monitoring and forensic analysis, etc., are further provided.

BACKGROUND ART

Microarray technology has been developing quickly since it first appeared in the 1990's (Fodor et al., *Science*, 251: 767–773 (1991)). Now as a representative category of biochip technology, microarray technology has been widely utilized in clinical diagnostics, disease mechanism research, drug discovery, environmental monitoring, functional genomics research etc. (Hacia et al., *Nature Genetics*, 14: 441–447 (1996); and Heller et al., *Proc. Natl. Acad. Sci. USA*, 94: 2150–2155 (1997)). Biological probes, such as oligonucleotides, DNA, RNA, peptides, proteins, cells, tissues, are immobilized on the surface of various substrate such as glass, silicon, nylon membrane etc. These probes represent particular information respectively. Sample is added into the reaction well in which the microarray is put to interact with immobilized probes. Sample may be labeled by isotope, fluorescent reagents, chemiluminescent reagents to facilitate the detection. According to different labeling methods, various detection methods can be used, such as confocal fluorescent scanner, low luminescence detector, isotope imager, etc.

To achieve high-throughput parallel analysis, high density microarrays have been developed on which several hundred thousand probes are immobilized. But in many cases, high density and high cost microarrays are not absolutely necessary. Moreover, high density microarrays do not necessarily mean high fidelity of detection signal because different probes on the microarray have subtle distinctions by nature. For example, if probes are DNA molecules, they may have different number of bases or different sequences, both of which contribute to the consequence of varied optimal hybridization conditions. Only under optimal hybridization conditions, mismatch ratio can be reduced to low level to facilitate the generation of accurate hybridization signals. Furthermore, the detection operation is inconvenient for most microarrays as they must be detected one at a time.

DISCLOSURE OF THE INVENTION

This invention provides an integrated microarray device which can be applied to multiple chemical and/or biological sample reactions and detections with high efficiency, high fidelity and low cost.

In one aspect, the invention provides an integrated microarray device, which device comprises a substrate comprising a plurality of distinct microlocations and a plurality of microarray chips, wherein the number of said microlocations equals to or is more than the number of said microarray chips. In preferred embodiments, the devices also comprise a temperature controller at some or all of the microlocations.

In another aspect, the invention provides a method for detecting interaction between a test moiety and a plurality of target moieties, which method comprises: a) providing an integrated microarray device, which device comprises a substrate comprising a plurality of distinct microlocations and a plurality of microarray chips, wherein the number of said microlocations equals to or is more than the number of said microarray chips, and a plurality of target moieties attached to said microarray chips; b) contacting a test moiety with said plurality of target moieties provided in step a); and c) detecting interaction between said test moiety and said plurality of target moieties.

In a preferred embodiment, the device provided herein includes a substrate, on which reaction wells are fabricated. In every reaction well a microarray chip is placed in. This microarray chip may be of a high, or low, preferably, a low density chip. In addition, a temperature controller is placed inside or outside every reaction well mentioned above. These temperature controllers can individually control the temperature in each reaction well. When fabricating microarray chips customarily made for such microarray device, probes are divided into different groups according to their respective melting temperatures ($T_m$ value). Probes with close enough melting temperature values are immobilized on one microarray chip; the chip is then put into one reaction well. Reaction temperature in different reaction well can be controlled individually by attached temperature controller. The reaction temperature in every well can be controlled exactly according to the $T_m$ value of probes immobilized so that false positive rate or detection error caused by the inappropriate temperature control can be reduced. The dimension of this microarray device corresponds to standard 96-well plate, 384-well plate or 1536-well plate. That is, the number of reaction wells and the distance between different wells are standardized. This design facilitates simple, high efficient and automatic manipulation such as sample handling and washing by robotics.

BRIEF DESCRIPTION OF THE DRAWINGS

In the drawings, the same reference numbers represent the same parts.

FIG. 2 is the three-dimensional schematic illustration of one unit in an exemplary integrated microarray device.

FIG. 3 schematically illustrates the electronic connection lines of the temperature controllers, as parts of an exemplary integrated microarray device.

MODES OF CARRYING OUT THE INVENTION

Figure 1:
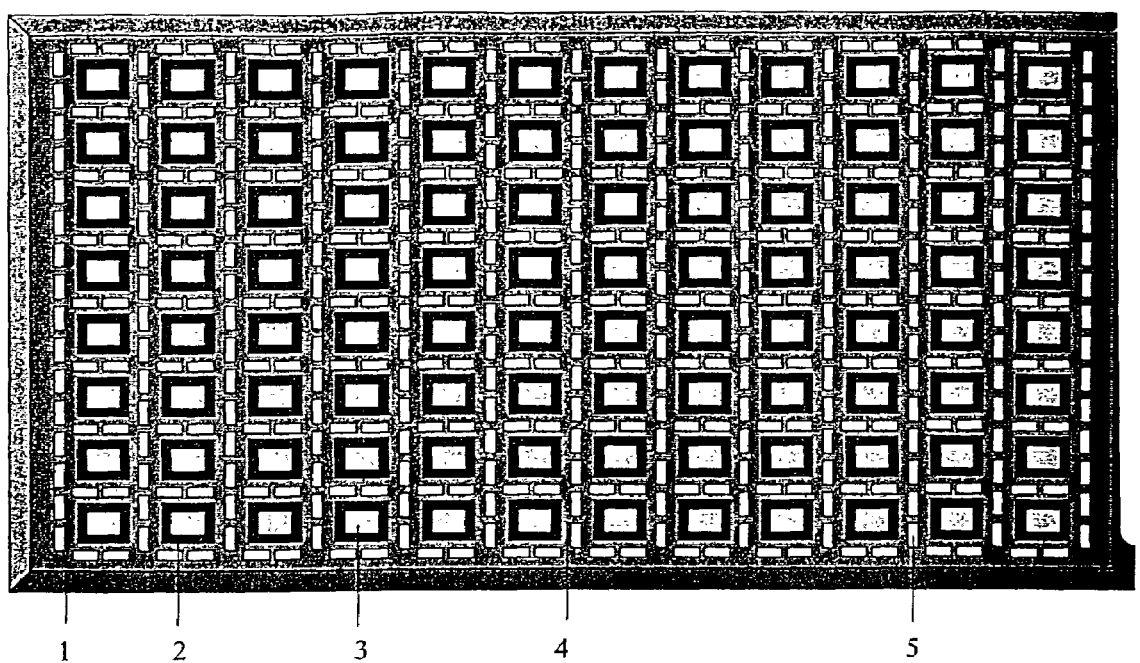
FIG. 1 is the top-view schematic illustration of an exemplary integrated microarray device.
Figure 4:
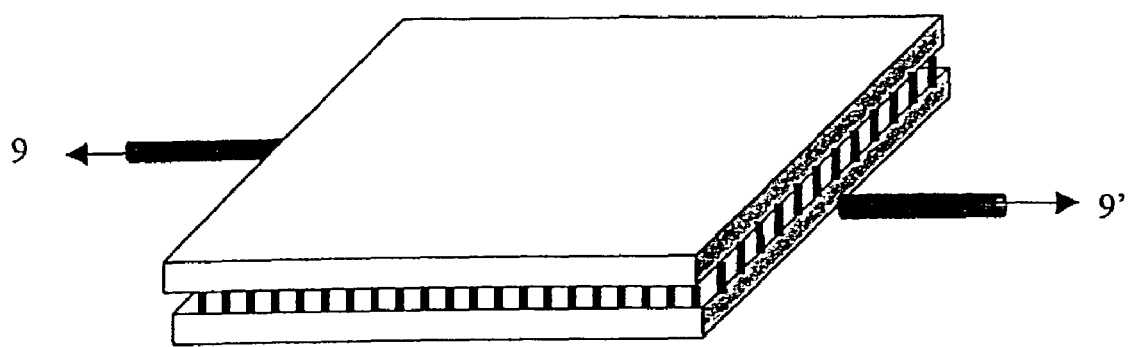
FIG. 4 is the structure schematic illustration of a semiconductor temperature controller used for microarray device of this invention.

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this section prevails over the definition that is incorporated herein by reference.

As used herein, "a" or "an" means "at least one" or "one or more."

As used herein, "microarray chip" refers to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips can vary considerably, e.g., from about 1 $mm^2$ to about 0.25 $m^2$. Preferably, the size of the chips is from about 4 $mm^2$ to about 25 $cm^2$ with a characteristic dimension from about 1 mm to about 5 cm. The chip surfaces may be flat, or not flat. The chips with non-flat surfaces may include channels or wells fabricated on the surfaces.

As used herein, "microlocations" refers to places that are within, on the surface or attached to the substrate wherein the microarray chips and/or other structures or devices are located.

As used herein, "distinct microlocations" means that the microlocations are sufficiently separated so that, if needed, reagents can be added and/or withdrawn and reactions can be conducted in one microlocation independently from another microlocation. It is not necessary that each microlocation is "distinct" from all other microlocations, although in certain embodiments, each microlocation can be "distinct" from all other microlocations.

As used herein, "microlocations are in a well format" means that there are indentations with suitable three dimensional shape at the microlocations so that microarray chips and/or other structures or devices such as temperature controllers, can be built or placed into.

As used herein, "microlocations is thermally insulated" means that the microlocations have certain structures or substances that can be used to adjust to and maintain temperature at a microlocation at a desired level independently from other microlocations or any place outside the microlocation.

As used herein, "moiety" encompasses both test moiety and target moiety. Non-limiting examples of moieties include cells, cellular organelles, viruses, particles, molecules, e.g., proteins, DNAs and RNAs, or an aggregate or complex thereof.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "bacteria" refers to small prokaryotic organisms (linear dimensions of around 1 micron) with non-compartmentalized circular DNA and ribosomes of about 70 S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are three main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to an obligate intracellular parasite of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungus" refers to a division of eucaryotic organisms that grow in irregular masses, without roots, stems, or leaves, and are devoid of chlorophyll or other pigments capable of photosynthesis. Each organism (thallus) is unicellular to filamentous, and possesses branched somatic structures (hyphae) surrounded by cell walls containing glucan or chitin or both, and containing true nuclei.

As used herein, "intracellular moiety" refers to any moiety that resides or is otherwise located within a cell, i.e., located in the cytoplasm or matrix of cellular organelle, attached to any intracellular membrane, resides or is otherwise located within periplasma, if there is one, or resides or is otherwise located on cell surface, i.e., attached on the outer surface of cytoplasm membrane or cell wall, if there is one.

As used herein, "macromolecule" refers to a molecule that, without attaching to another molecule, is capable of generating an antibody that specifically binds to the macromolecule.

As used herein, "small molecule" refers to a molecule that, without forming homo-aggregates or without attaching to a macromolecule or adjuvant, is incapable of generating an antibody that specifically binds to the small molecule. Preferably, the small molecule has a molecular weight that is about or less than 10,000 daltons. More preferably, the small molecule has a molecular weight that is about or less than 5,000 dalton.

As used herein, "vitamin" refers to a trace organic substance required in certain biological species. Most vitamins function as components of certain coenzymes.

As used herein, "lipid" refers to water-insoluble, oily or greasy organic substances that are extractable from cells and tissues by nonpolar solvents, such as chloroform or ether.

As used herein, a "receptor" refers to a molecule that has an affinity for a given ligand. Receptors may be naturally-occurring or synthetic molecules. Receptors may also be referred to in the art as anti-ligands. As used herein, the receptor and anti-ligand are interchangeable. Receptors can be used in their unaltered state or as aggregates with other species. Receptors may be attached, covalently or noncovalently, or in physical contact with, to a binding member, either directly or indirectly via a specific binding substance or linker. Examples of receptors, include, but are not limited to: antibodies, cell membrane receptors surface receptors and internalizing receptors, monoclonal antibodies and antisera reactive with specific antigenic determinants [such as on viruses, cells, or other materials], drugs, polynucleotides, nucleic acids, peptides, cofactors, lectins, sugars, polysaccharides, cells, cellular membranes, and organelles.

As used herein, "antibody" includes antibody fragments, such as Fab fragments, which are composed of a light chain and the variable region of a heavy chain.

As used herein, "humanized antibodies" refer to antibodies that are modified to include "human" sequences of amino acids so that administration to a human will not provoke an immune response. Methods for preparation of such antibodies are known. For example, the hybridoma that expresses the monoclonal antibody is altered by recombinant DNA techniques to express an antibody in which the amino acid composition of the non-variable regions is based on human antibodies. Computer programs have been designed to identify such regions.

As used herein, "a group of structurally and/or functionally related proteins" refers to a group of proteins, at their natural status, that are structurally linked, located at the same cellular locations, e.g., cellular organelles, located in the same tissues or organs, expressed and/or be functional in the same biological stages, e.g., a particular cell cycle stage or developmental stage, or expressed and/or be functional in the same biological pathway, e.g., a particular metabolism pathway, signal transduction pathway, etc. The "group of structurally and/or functionally related proteins" need only include at least two proteins belonging to the same group. The "group of structurally and/or functionally related proteins" can preferably include more than two proteins belonging to the same group, e.g., a majority of or even all the proteins belonging to the same group.

As used herein, "nutrient or storage protein" refers to a protein that is used by the cell as the nutrient source or storage form for such nutrient. Non-limiting examples of nutrient or storage proteins include gliadin, ovalbumin, casein, and ferritin.

As used herein, "contractile or motile protein" refers to a protein that endows cells and organisms with the ability to contract, to change shape, or to move about. Non-limiting examples of contractile or motile proteins include actin, myosin, tubulin and dynein.

As used herein, "structural protein" refers to a protein that serves as supporting filaments, cables, or sheets to give biological structures strength or protection. Non-limiting examples of structural proteins include keratin, fibroin, collagen, elastin and proteoglycans.

As used herein, "defense protein" refers to a protein that defends organisms against invasion by other species or protect them from injury. Non-limiting examples of defense proteins include antibodies, fibrinogen, thrombin, botulinus toxin, diphtheria toxin, snake venoms and ricin.

As used herein, "regulatory protein" refers to a protein that helps regulate cellular or physiological activity. Non-limiting examples of regulatory proteins include insulin, growth hormones, corticotropin and repressors.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). The sample may also be a mixture of target protein containing molecules prepared in vitro.

As used herein, "a group of structurally and/or functionally related enzymes" refers to a group of enzymes, at their natural status, that are structurally linked, located at the same cellular locations, e.g., cellular organelles, located in the same tissues or organs, expressed and/or be functional in the same biological stages, e.g., a particular cell cycle stage or developmental stage, or expressed and/or be functional in the same biological pathway, e.g., a particular metabolism pathway, signal transduction pathway, or act as a regulator for a pathway activation or a biological function, etc. The "group of structurally and/or functionally related enzymes" need only include at least two enzymes belonging to the same group. The "group of structurally and/or functionally related enzymes" can preferably include more than two enzymes belonging to the same group, e.g., a majority of or even all the enzymes belonging to the same group.

As used herein, "expressed in a tissue or organ specific manner" refers to a gene expression pattern in which a gene is expressed, either transiently or constitutively, only in certain tissues or organs, but not in other tissues or organs.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein: "stringency of hybridization" in determining percentage mismatch is as follows:
1) high stringency: 0.1×SSPE, 0.1% SDS, 65° C.;
2) medium stringency: 0.2×SSPE, 0.1% SDS, 50° C. (also referred to as moderate stringency); and 3) low stringency: 1.0×SSPE, 0.1% SDS, 50° C.

It is understood that equivalent stringencies may be achieved using alternative buffers, salts and temperatures.

As used herein, "gene" refers to the unit of inheritance that occupies a specific locus on a chromosome, the existence of which can be confirmed by the occurrence of different allelic forms. Given the occurrence of split genes, gene also encompasses the set of DNA sequences (exons) that are required to produce a single polypeptide.

As used herein, "gene chip" refers to an array of oligonucleotides immobilized on a surface that can be used to screen an RNA sample (after reverse transcription) and thus a method for rapidly determining which genes are being expressed in the cell or tissue from which the RNA came.

As used herein, "RNA" refers to ribose units joined in the 3' and 5' positions through a phosphodiester linkage with a purine or pyrimidine base attached to the 1' position.

As used herein, "protein" refers to a linear polymer of amino acids joined by peptide bonds in a specific sequence. As used herein, "protein" also encompasses polypeptide, oligopeptide and peptide.

B. Integrated Microarray Devices

In one aspect, the invention provides an integrated microarray device, which device comprises a substrate comprising a plurality of distinct microlocations and a plurality of microarray chips, wherein the number of said microlocations equals to or is more than the number of said microarray chips.

Any suitable substrate can be used in the present integrated microarray device. In a preferred embodiment, the substrate comprises silicon, e.g., silicon dioxide or silicon nitride, plastic, glass, ceramic, rubber, polymer or a composite thereof. The substrate can comprise a surface that is hydrophobic or hydrophilic. In addition, the substrate can comprise a surface that is porous or nonporous.

The microlocations can be made within, on or attached to the substrate by any suitable methods. For example, the microlocations can be produced directly as part of the substrate. Alternatively, the substrate can be produced first and the microlocations are subsequently be made within, on or attached to the substrate. In a preferred embodiment, the microlocations and/or the microarray chips are fabricated on the substrate.

The device can comprise any suitable number of microlocations. For example, the device can comprise $(12)_n$ number of microlocations, wherein n is an integer that is at least 1. Preferably, n is 8, 32 or 128. The microlocations can be evenly or unevenly distributed on the substrate. Preferably, the number microlocations and the distance among the microlocations correspond to a standard microtiter plate, e.g., 96-, 384-, or 1536-well plate.

The microlocations can be in any suitable format. For example, the microlocations can be made within the substrate or can be made on the surface or above the surface of the substrate. Preferably, the microlocations are in a well format or a thermally insulated flat surface format. The device can comprise $(12)_n$ number of wells, wherein n is an integer that is at least 1. Preferably, the device comprises 96, 384 or 1,536 wells. The wells can have any suitable three dimensional shapes or geometries. For example, the top, middle and/or bottom portion of the wells can be circle, oval, square, rectangle, triangle and other irregular shape(s). The top, middle and/or bottom portion of the wells can have the same or different shapes and/or areas. The device can comprise wells having identical or different two-dimensional or three-dimensional shapes or geometries.

The microlocations can be in fluid contact with a fluid source or fluid passage outside the device. Any number or percentage of the microlocations, e.g., 50% of the microlocations, can be in fluid contact with a fluid source or fluid passage outside the device. Preferably, all of the microlocations are in fluid contact with a fluid source or fluid passage outside the device. In a specific embodiment, at least two of the microlocations can be in fluid contact with each other. Any number or percentage of the microlocations, e.g., 50% of the microlocations, can be in fluid contact with each other. Preferably, all of the microlocations are in fluid contact with each other. The microlocations can be made in fluid contact with a fluid source or fluid passage outside the device and/or with each other using any suitable structures, e.g., microfluidic channels.

In a specific embodiment, at least one of the microlocations, e.g., wells, can be thermally insulated. Any number or percentage of the microlocations, e.g., 50% of the microlocations, can be thermally insulated. Preferably, all of the microlocations can be thermally insulated. The microlocations can be thermally insulated using any suitable structures or materials. For example, the microlocation(s) can be thermally insulated by inert gas, e.g., air. In a preferred embodiment, some wells or all of the wells are connected to each other by thin girders and thermally insulated by the air contained between the walls of the adjacent wells.

The number of the microlocations in the present device should be more than or equal to the number of the microarray chips. Preferably, each of the microlocations in the device comprises a microarray chip.

Any suitable microarray chips can be used in the present integrated microarray device. For example, microarray chips suitable for nucleic acid analysis, e.g., gene chip, and/or protein chip, antibody chip, can be used in the present device (See generally, Ausubel et al., *Current Protocols in Molecular Biology*, §22, John Wiley & Sons, Inc. (2000); and Schena (Ed.), *Microarray Biochip technology*, Eaton Publishing Company/Bio Techniques Books Division (2000)). In a specific embodiment, the microarray chips disclosed in the following U.S. Pat. Nos. can be used in the present device: U.S. Pat. Nos. 6,245,511, 6,215,894, 6,142,681, 6,101,946, 6,004,755, 5,930,117, 5,928,437 and 5,716,459.

The microarray chips can have any desirable densities. The microarray chips can have identical or different densities. In a specific embodiment, the microarray chips have a density of $(100)_n$ spots/cm$^2$, wherein n is an integer that is at least 1. Preferably, at least one of the microarray chips has a density that is less than or equals to 400 spots/cm$^2$. However, any number or percentage of the microarray chips, e.g., 50% of the microarray chips, can have a density that is less than or equals to 400 spots/cm$^2$. More preferably, all of the microarray chips have a density that is less than or equals to 400 spots/cm$^2$.

In another specific embodiment, at least one of the microarray chips has attached thereto a plurality of moieties. The microarray chip(s) can have attached thereto a plurality of moieties on facing up or down direction. The moieties can be attached to the microarray chip(s) using any suitable methods. The moieties can be attached to the microarray chip(s) covalently, non-covalently, through specific or non-specific linkage, can be attached directly or through a linker. The linker can be sensitive to certain treatment, such as physical, chemical or enzymatic treatment.

Any suitable moieties can be attached to the microarray chip(s). The moieties can be pure substances or composite materials, can be chemical or biological materials, or can be synthetic or isolated/purified from biological sources or samples. Exemplary moieties include cells, cellular organelles, viruses, molecules and an aggregate or complex thereof.

Non-limiting examples of cells include animal, plant, fungi, bacteria, recombinant or cultured cells. Animal, plant, fungus, bacterium cells can be derived from any genus or subgenus of the Animalia, Plantae, fungus or bacterium kingdom. Cells derived from any genus or subgenus of ciliates, cellular slime molds, flagellates and microsporidia can also be attached to the microarray chip(s). Cells derived from birds such as chickens, vertebrates such as fish and mammals such as mice, rats, rabbits, cats, dogs, pigs, cows, ox, sheep, goats, horses, monkeys and other non-human primates, and humans can be attached to the microarray chip(s).

For animal cells, cells derived from a particular tissue or organ can be attached to the microarray chip(s). For example, connective, epithelium, muscle or nerve tissue cells can be used. Similarly, cells derived from an accessory organ of the eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subformical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl can be used. Preferably, cells derived from an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc can be used. Further, cells derived from any plants, fungi such as yeasts, bacteria such as eubacteria or archaebacteria can be used. Recombinant cells derived from any eucaryotic or prokaryotic sources such as animal, plant, fungus or bacterium cells can also be used. Body fluid such as blood, urine, saliva, bone marrow, sperm or other ascitic fluids, and subfractions thereof, e.g., serum or plasma, can also be used.

Attachable cellular organelles include nucleus, mitochondria, chloroplasts, ribosomes, ERs, Golgi apparatuses, lysosomes, proteasomes, secretory vesicles, vacuoles or microsomes. Attachable viruses, whether intact viruses or any viral structures, e.g., viral particles, in the virus life cycle can be derived from viruses such as Class I viruses, Class II viruses, Class III viruses, Class IV viruses, Class V viruses or Class VI viruses.

Attachable intracellular moiety include any moiety that resides or is otherwise located within a cell, i.e., located in the cytoplasm or matrix of cellular organelle; attached to any intracellular membrane; resides or is otherwise located within periplasma, if there is one; or resides or is otherwise located on cell surface, i.e., attached on the outer surface of cytoplasm membrane or cell wall, if there is one. Any desired intracellular moiety can be isolated from the target cell(s). For example, cellular organelles, molecules or an aggregate or complex thereof can be isolated. Non-limiting examples of such cellular organelles include nucleus, mitochondria, chloroplasts, ribosomes, ERs, Golgi apparatuses, lysosomes, proteasomes, secretory vesicles, vacuoles or microsomes, membrane receptors, antigens, enzymes and proteins in cytoplasm.

Attachable molecules can be inorganic molecules such as ions, organic molecules or a complex thereof. Non-limiting examples of attachable ions include sodium, potassium, magnesium, calcium, chlorine, iron, copper, zinc, manganese, cobalt, iodine, molybdenum, vanadium, nickel, chromium, fluorine, silicon, tin, boron or arsenic ions. Non-limiting examples of attachable organic molecules include amino acids, peptides, proteins, nucleosides, nucleotides, oligonucleotides, nucleic acids, vitamins, monosaccharides, oligosaccharides, carbohydrates, lipids or a complex thereof.

Any amino acids can be attached to the microarray chip(s). For example, a D- and a L-amino-acid can be attached. In addition, any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V) can be attached.

Any proteins or peptides can be attached to the microarray chip(s). For example, enzymes, transport proteins such as ion channels and pumps, nutrient or storage proteins, contractile or motile proteins such as actins and myosins, structural proteins, defense protein or regulatory proteins such as antibodies, hormones and growth factors can be attached. Proteineous or peptidic antigens can also be attached.

Any nucleic acids, including single-, double and triple-stranded nucleic acids, can be attached to the microarray chip(s). Examples of such nucleic acids include DNA, such as A-, B- or Z-form DNA, and RNA such as mRNA, tRNA and rRNA.

Any nucleosides can be attached to the microarray chip(s). Examples of such nucleosides include adenosine, guanosine, cytidine, thymidine and uridine. Any nucleotides can be attached to the microarray chip(s). Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Any vitamins can be attached to the microarray chip(s). For example, water-soluble vitamins such as thiamine, riboflavin, nicotinic acid, pantothenic acid, pyridoxine, biotin, folate, vitamin $B_{12}$ and ascorbic acid can be attached. Similarly, fat-soluble vitamins such as vitamin A, vitamin D, vitamin E, and vitamin K can be attached.

Any monosaccharides, whether D- or L-monosaccharides and whether aldoses or ketoses, can be attached to the microarray chip(s). Examples of monosaccharides include triose such as glyceraldehyde, tetroses such as erythrose and threose, pentoses such as ribose, arabinose, xylose, lyxose and ribulose, hexoses such as allose, altrose, glucose, mannose, gulose, idose, galactose, talose and fructose and heptose such as sedoheptulose.

Any lipids can be attached to the microarray chip(s). Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

In a specific embodiment, at least two of the microarray chips can have attached thereto a plurality of moieties. However, any number or percentage of the microarray chips, e.g., 50% of the microarray chips, can have attached thereto a plurality of moieties. Preferably, each of the microarray chips has attached thereto a plurality of moieties. The microarray chips can have attached thereto same type or different type of moieties.

In another specific embodiment, at least one of the microlocations can comprise a temperature controller. However, any number or percentage of the microlocations, e.g., 50% of the microlocations, can comprise a temperature controller. Preferably, each of the microlocations comprises a temperature controller. More preferably, each of the microlocations comprises a microarray chip and a temperature controller. Some, e.g., 50% of the temperature controllers, can be individually controllable. Preferably, each of the temperature controller is individually controllable.

Any suitable temperature controller can be used in the present device. For example, a resistive heater, a bidirectional semiconductor temperature controller, a ceramic heater or an infrared heater can be used.

The substrate in the present device can be an unitary unit. Alternatively, the substrate can be an assembled unit, which can be disassembled into at least two parts.

C. Detecting Methods

In another aspect, the invention provides a method for detecting interaction between a test moiety and a plurality of target moieties, which method comprises: a) providing an integrated microarray device, which device comprises a substrate comprising a plurality of distinct microlocations and a plurality of microarray chips, wherein the number of said microlocations equals to or is more than the number of said microarray chips, and a plurality of target moieties attached to said microarray chips; b) contacting a test moiety with said plurality of target moieties provided in step a); and c) detecting interaction between said test moiety and said plurality of target moieties. The present methods can be used in any suitable fields including prognosis, diagnosis, drug screening, environmental monitoring, etc.

Any suitable integrated microarray device, including the devices described in the above Section B, can be used in the present method. In a specific embodiment, the integrated microarray device comprises a substrate comprising a plurality of distinct microlocations and each of the microlocations comprises a microarray chip and a temperature controller.

The present methods can be used to detect any interaction(s) among moieties selected from the group consisting of a cell, a cellular organelle, a virus, a molecule and an aggregate or complex thereof. For example, the present methods can be used to detect interactions between or among macromolecules, such as DNA-DNA, DNA-RNA, RNA-RNA, DNA-protein, RNA-protein and protein-protein, etc., interactions. The present methods can also be used to detect macromolecule-small molecule or small molecule-small molecule interactions. The present methods can also be used to detect more complex interactions including interactions among more than two moieties. When DNA-DNA, DNA-RNA, RNA-RNA interactions are to be detected, the contacting, i.e., hybridizing, step, can be conducted under suitable condition, e.g., under low, middle or high stringency.

The interaction between said test moiety and said plurality of target moieties can be detected by any suitable methods. For example, the test moiety and/or target moieties can be labeled to facilitate detection. Any suitable label can be used. Exemplary labels include a radioactive, a fluorescent, a chemical, an enzymatic, a luminescent and a FRET (fluorescence resonance energy transfer) label. The luminescent label can be a chemiluminescent label or a bioluminescent label. The labels can be attached or conjugated, directly or indirectly, to the test moiety alone, the target moiety alone, or on both. The read-out can be a positive or a negative signal. Any suitable assay formats, including sandwich or competitive formats, can be used.

In a preferred embodiment, the present methods are used to detect interaction between or among a test moiety and a plurality of genes, gene fragments or their encoded products. More preferably, the plurality of target genes, gene fragments or their encoded products are involved in a biological pathway, belong to a group of proteins with identical or similar biological function, expressed in a stage of cell cycle, expressed in a cell type, expressed in a tissue type, expressed in an organ type, expressed in a developmental stage, proteins whose expression and/or activity is altered in a disease or disorder type or stage, or proteins whose expression and/or activity is altered by drug or other treatments.

The present methods can be used in detecting interaction between or among a single test moiety or substance and a plurality of target moieties. Preferably, the present methods are used in high-throughput mode, i.e., in detecting interaction between or among a plurality of test moieties or substances and a plurality of target moieties. The interaction between a plurality of test moieties or substances and a plurality of target moieties can be detected simultaneously or sequentially.

D. Description of Exemplary Devices

FIG. 1 is the top-view schematic illustration of an exemplary integrated microarray device. This device includes a substrate 1. Substrate 1 can be made of plastics, glass, silicon, ceramics etc., and can be porous or nonporous, rigid or flexible.

Multiple reaction wells 2 are fabricated on the substrate 1 by appropriate methods such as etching. Then every reaction well is introduced with a microarray chip 3. The number of reaction wells and distance between different wells can be modified according to the practical need. If possible, it is recommended that the parameters (such as the number of reaction wells or distance between or among different wells) of wells be identical to a standard plate, such as standard 96-well plate, 384-well plate or 1536-well plate, to facilitate automated manipulation (such as sample handling or washing) by robotics. In the example shown in FIG. 1, the dimensional parameter of the microarray device is identical to a standard 96-well plate. That is, there are 96 reaction wells 2 on the substrate 1, and the distance from one well to the adjacent well is 9 mm, identical to the distance between adjacent wells on a standard 96-well plate.

The three dimensional schematic illustration of a well unit of the microarray device is shown in FIG. 2 in which a reaction well 2 and attached microarray chip 3 are drawn. The shape of the top port of the reaction well is quadrate. The diameter of its circumcircle should be smaller than or equal to that of a standard 96-well plate. And the shape of microarray chip 3 which is placed in the reaction well 2 is quadrate too. In this preferred embodiment, the quadrate shape of reaction well 2 and microarray chip 3 ensures the correct positioning orientation of microarray chip 3. Skilled artisans will understand that the shape is not limited to quadrate. Other shapes such as orbicular can also be adopted to shape the reaction well 2 and microarray chip 3. For microarray chip 3, the surface on which probes are immobilized may face up (FIG. 2A) or face down (FIG. 2B). The bottom of reaction well 2 may be sealed and reagents (e.g., hybridization reagents or washing reagents) could then be added in or moved out from top (FIG. 2A). Alternatively, the bottom of the device can be designed to be partially open, namely at least one microfluidic channel will be fabricated on the bottom to facilitate the addition or removal of reagents (hybridization reagents or washing reagents) from the bottom (FIG. 2B). Reaction well 2 may be fabricated as a whole device, or it may include at least two dissembled parts. For example, if needed, the bottom of the reaction well can be pulled down to undergo the subsequent detection. The depth of reaction well 2 can be modified according to the thickness of microarray chip 3 and the reaction volume can be varied from several hundreds micrometers to several centimeters.

When the present microarray device is applied to detecting biological or pharmaceutical samples, probes can be divided into different groups according to their properties such as number of bases or sequence of probes. Probes from the same group are then immobilized on the same microarray chip 3 in a reaction well 2. Probes can be cDNA, oligonucleotides, antigens or antibodies, receptors, polypeptides, cells or tissues. The substrate of microarray chip 3 can be silicon, glass or nylon membrane etc. Immunobilization methods for probes can be absorption, covalent binding, entrapment etc. (Beattie et al., *Molecular Biotechnology*, 4:213–225, (1995); and Subramanian et al., *Enzyme & Microbial Technol*, 24:26–34, (1999)).

In many cases such as diagnosis of one kind of disease, screening one kind of drug or researching some specific genes' functions, microarray with high density is not absolutely necessary. Microarray chip 3 of the present device may be of low density microarray chip on which only several tens or several hundreds probes are immobilized. The corresponding fabrication costs can be decreased a lot by using low density microarray chips. On the other hand, the microarray device of this invention includes multiple units (for example, the number of units may be 96, 384 or 1536). Though the number of probes in every reaction well is not high, the number of probes in all these reaction wells together may range from several thousands to several hundreds thousands to achieve high-throughput analysis and also provide middle sized density.

To control temperature in every reaction well 2, illustrated by FIG. 2, a temperature controller 6 is attached to every reaction well 2. FIG. 3 illustrates an exemplary connection between different temperature controllers 6. There are two lines 9 and 9' stretching from every temperature controller 6 connected to anode and cathode of power supply respectively. Individual control of temperature of different reaction wells 2 may be achieved by addressable activation/inactivation of different temperature controllers 6.

Temperature controller 6 may simply be a resistor applied to heat reaction well 2. It may be attached to the bottom of reaction well 2. If substrate is made of silicon, microfabrication technology may be applied to etch the opposite face of reaction well 2, then deposit a layer of metal (such as copper) on silicon to fabricate temperature controller 6. And the bottom of reaction well 2 is fabricated as thin as possible to facilitate heat transfer between temperature controller 6 and microarray chip 3 in the reaction well 2. Alternatively, temperature controller 6 may be a bidirectional semiconductor temperature controller. On the one hand, this bidirectional semiconductor temperature controller may heat reaction well 2; on the other hand, it may cool reaction well 2 when its temperature is higher than environmental temperature (such as 50° C.). This bidirectional semiconductor temperature controller may be attached to the bottom of reaction well 2. Temperature controller 6 may also be put into reaction well 2 by the way illustrated by FIG. 2B. Temperature controller 6 may be bond to microarray chip 3 by mechanical rabbet joint. Alternatively, the binding may be achieved by introducing a layer of liquid, which would not take part in reaction or evaporate during the reaction. The binding force is surface tension between the surface of this liquid and that of the temperature controller 6. Moreover, the introduced liquid would also facilitate the heat transfer.

Skilled artisans will understand that any kinds of temperature controllers, not just limited to resistors or bidirectional semiconductor temperature controllers, can be applied to temperature controller 6 of this invention. For example, ceramics heater can be applied to temperature controller 6 by attaching it directly to the bottom of reaction well 2. Alternatively, infrared heating can be applied by using the non-contact infrared waves. The connecting way between temperature controller 6 and computer to achieve addressable control of temperature controller 6 is not limited to the way mentioned above. Any appropriate ways for temperature control can be applied.

In the preferred embodiment of the device in this invention illustrated by FIG. 1 and FIG. 2, through holes fabricated on the insulation wall between every reaction well, different reaction wells are connected to each other by thin girders to facilitate heat insulation between different reaction well 2. The size of the hole should be as large as possible as long as the tightness of the system is enough. For example, if the substrate is made of plastics, the size of every pore may be 3×2 millimeters. According to different materials used, different fabrication methods may be applied, such as laser ablation (Simpson et al., *Proc. Natl. Acad. Sci. USA*, 95:2256–2261 (1998)), molding (Becker et al., *Sensors Update*, 3:208–238 (1998); and Delamarche et al., *J. Am. Chem. Soc.*, 120:500–508 (1998)), and embossing (Kopp et al., *Current Opinion in Chemical Biology*, 1:410–419 (1997)).

When the present microarray device is applied to biochemical reactions, a cover-slip may be used to cover the sample solution after the solution is added to microarray chip 3 in the reaction well 2. It will help avoiding evaporation of the sample. And the size of cover-slip is flexible according to microarray chip's size (no larger than the area of microarray chip 3). Alternatively, as illustrated by FIG. 2, high boiling point hydrophobic organic reagents (such as mineral oil) can be applied to block the reaction system. The reagent volume should be decided by the sample volume and the area of microarray chip.

As illustrated in FIG. 2B, when microarray chip 3 is placed in a face-down position into the reaction well, hydrophobic and bio-compatible liquid 10 can be added to fill the reaction well 2. And this liquid's specific gravity and boiling point should be higher than water to allow sample floating above the liquid to interact with probes attached on the microarray chip 3. After reaction, liquid 10 can be drawn out through microfluidic channel fabricated on the bottom of reaction well 2, and washing solution can be added in.

The detection of reaction results can be completed by a charge coupled device (CCD) or isotope imager. It should be decided upon by the labeling methods applied to samples. Integrated microarray device can be placed on the microscope stage, which can move with predetermined distance steadily. The detector can detect one microarray chip 3 at one time, then the motorized can move to the position of next reaction well to be scanned. Such detection devices are cheap, effective, simple and easy to use so they are possible to be applied in small hospitals or laboratories.

REFERENCES CITED

Beattie W. G. et al., "Hybridization of DNA targets to glass-tethered oligonucleotide probes", Molecular Biotechnology 4: 213–225, 1995

Becker H. et al., "Integrated capillary electrophoresis for chemical analysis", in Baltes H. et al. (Eds), Sensors Update, Vol.3, VCH Weiheim 208–238, 1998

Delamarche E. et al., "Microfluidic networks for chemical patterning of substrate: Design and application to bioassays", J. Am. Chem. Soc. 120: 500–508, 1998

Fodor S. P. A. et al., "Light-directed spatially addressable parallel chemical synthesis", Science 251: 767–773, 1991

Hacia J. G. et al., "Detection of heterozygous mutations in BRCA1 using high density oligonucleotide arrays and two-colour fluorescence analysis", Nature Genetics 14: 441–447, 1996;

Heller R. A. et al., "Discovery and analysis of inflammatory disease-related genes using cDNA microarrays", Proc. Natl. Acad. Sci. USA 94: 2150–2155, 1997

Kopp M. U. et al., "Developments in technology and applications of Microsystems", Current Opinion in Chemical Biology 1: 410–419, 1997, Simpson P. C. et al., "High-throughput genetic analysis using microfabricated 96-sample capillary array electrophoresis microplates", Proc. Natl. Acad. Sci. USA 95: 2256–2261, 1998

Subramanian A. et al., "Comparison of techniques for enzyme immobilization on silicon supports", Enzyme & Microbial Technol. 24: 26–34, 1999.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

What is claimed is:

1. A method for detecting interaction between a test moiety and a plurality of target moieties, which method comprises:
a) providing an integrated microarray device, which device comprises a substrate comprising a plurality of distinct microlocations and a plurality of microarray chips, wherein the number of said microlocations equals to or is more than the number of said microarray chips, and a plurality of target moieties attached to said microarray chips, and wherein the microlocations are in a well format comprising a plurality of wells wherein all of the wells are defined by inside and outside walls connected by thin girders wherein the thin girders and inside and outside walls of the wells form a space to contain an inert gas and thermally insulate adjacent wells from each other;
b) contacting a test moiety with said plurality of target moieties provided in step a); and
c) detecting interaction between said test moiety and said plurality of target moieties.

2. The method of claim 1, wherein the integrated microarray device comprises a substrate comprising a plurality of distinct microlocations and each of the microlocations comprises a microarray chip and a temperature controller.

3. The method of claim 1, wherein the interaction being detected are interaction(s) among moieties selected from the group consisting of a cell, a cellular organelle, a virus, a molecule and an aggregate or complex thereof.

4. The method of claim 1, wherein the plurality of target moieties is a plurality of genes, gene fragments or their encoded products.

5. The method of claim 4, wherein the plurality of genes, gene fragments or their encoded products are involved in a biological pathway, belong to a group of proteins with identical or similar biological function, expressed in a stage of cell cycle, expressed in a cell type, expressed in a tissue type, expressed in an organ type, expressed in a developmental stage, proteins whose expression and/or activity is altered in a disease or disorder type or stage, or proteins whose expression and/or activity is altered by drug or other treatments.

6. The method of claim 1, wherein interaction between a plurality of target moieties and a plurality of target moieties are detected.

7. The method of claim 1, wherein interaction between a plurality of target moieties and a plurality of target moieties are detected simultaneously or sequentially.

8. The method of claim 1, wherein the substrate comprises silicon, plastic, glass, ceramic, rubber, polymer or a composite thereof.

9. The method of claim 8, wherein the silicon is silicon dioxide or silicon nitride.

10. The method of claim 1, wherein the substrate comprises a surface that is hydrophobic or hydrophilic.

11. The method of claim 1, wherein the substrate comprises a surface that is porous or nonporous.

12. The method of claim 1, wherein the microlocations and/or the microarray chips are fabricated on the substrate.

13. The method of claim 1, which comprises $(12)_n$ number of microlocations, wherein n is an integer that is at least 1.

14. The method of claim 1, wherein the microlocations are evenly or unevenly distributed on the substrate.

15. The method of claim 1, wherein the number of microlocations and the distance among the microlocations correspond to a standard microtiter plate.

16. The method of claim 1, wherein the microlocations are in a thermally insulated flat surface format.

17. The method of claim 16, which comprises $(12)_n$ number of wells, wherein n is an integer that is at least 1.

18. The method of claim 16, which comprises 96, 384 or 1,536 wells.

19. The method of claim 16, wherein the wells have a geometry selected from the group consisting of circle, oval, square, rectangle, triangle and other irregular shape(s).

20. The method of claim 16, wherein the wells have identical or different shapes.

21. The method of claim 1, wherein at least one of the microlocations is in fluid contact with a fluid source or fluid passage outside the device.

22. The method of claim 1, wherein all of the microlocations are in fluid contact with a fluid source or fluid passage outside the device.

23. The method of claim 1, wherein at least two of the microlocations are in fluid contact with each other.

24. The method of claim 1, wherein all of the microlocations are in fluid contact with each other.

25. The method of claim 1, wherein each of the microlocations comprises a microarray chip.

26. The method of claim 1, wherein the microarray chips have identical or different densities.

27. The method of claim 1, wherein the microarray chips have a density of $(100)_n$ spots/cm$^2$, wherein n is an integer that is at least 1.

28. The method of claim 1, wherein at least one of the microarray chips has a density that is less than or equals to 400 spots/cm$^2$.

29. The method of claim 1, wherein all of the microarray chips have a density that is less than or equals to 400 spots/cm$^2$.

30. The method of claim 1, wherein at least one of the microarray chips has attached thereto a plurality of moieties.

31. The method of claim 30, wherein the microarray chip(s) has attached thereto a plurality of moieties on facing up or down direction.

32. The method of claim 30, wherein each of the moieties is selected from the group consisting of a cell, a cellular organelle, a virus, a molecule and an aggregate or complex thereof.

33. The method of claim 32, wherein the cell is selected from the group consisting of an animal cell, a plant cell, a fungus cell, a bacterium cell, a recombinant cell and a cultured cell.

34. The method of claim 32, wherein the cellular organelle is selected from the group consisting of a nuclei, a mitochondrion, a chloroplast, a ribosome, an ER, a Golgi apparatus, a lysosome, a proteasome, a secretory vesicle, a vacuole and a microsome.

35. The method of claim 32, wherein the molecule is selected from the group consisting of an inorganic molecule, an organic molecule and a complex thereof.

36. The method of claim 35, wherein the inorganic molecule is an ion selected from the group consisting of a sodium, a potassium, a magnesium, a calcium, a chlorine, an iron, a copper, a zinc, a manganese, a cobalt, an iodine, a molybdenum, a vanadium, a nickel, a chromium, a fluorine, a silicon, a tin, a boron and an arsenic ion.

37. The method of claim 35, wherein the organic molecule is selected from the group consisting of an amino acid, a peptide, a protein, a nucleoside, a nucleotide, an oligonucleotide, a nucleic acid, a vitamin, a monosaccharide, an oligosaccharide, a carbohydrate, a lipid and a complex thereof.

38. The method of claim 1, wherein at least two of the microarray chips have attached thereto a plurality of moieties.

39. The method of claim 38, wherein each of the microarray chips has attached thereto same type or different type of moieties.

40. The method of claim 1, wherein each of the microarray chips has attached thereto a plurality of moieties.

41. The method of claim 1, wherein at least one of the microlocations comprises a temperature controller.

42. The method of claim 41, wherein each of the microlocations comprises a temperature controller.

43. The method of claim 41, wherein each of the temperature controller is individually controllable.

44. The method of claim 41, wherein the temperature controller is selected from the group consisting of a resistive heater, a bidirectional semiconductor temperature controller, a ceramic heater and an infrared heater.

45. The method of claim 1, wherein the substrate is an unitary unit.

46. The method of claim 1, wherein the substrate is an assembled unit, which can be disassembled into at least two parts.

* * * * *